(12) United States Patent
Saadi et al.

(10) Patent No.: US 11,120,901 B2
(45) Date of Patent: Sep. 14, 2021

(54) METHOD FOR CALCULATING THE ACTIVITY OF A USER

(71) Applicant: WITHINGS, Issy les Moulineaux (FR)

(72) Inventors: Rachid Saadi, Plaisir (FR); Nadine Buard, Meudon (FR); Cedric Hutchings, Issy les Moulineaux (FR)

(73) Assignee: WITHINGS, Issy les Molineaux (FR)

( * ) Notice: Subject to any disclaimer, the term of this patent is extended or adjusted under 35 U.S.C. 154(b) by 952 days.

(21) Appl. No.: 14/717,801

(22) Filed: May 20, 2015

(65) Prior Publication Data

US 2015/0335291 A1 Nov. 26, 2015

(30) Foreign Application Priority Data

May 20, 2014 (FR) ..................................... 1454498

(51) Int. Cl.
*A61B 5/00* (2006.01)
*G01P 15/02* (2013.01)
*G01C 22/00* (2006.01)
*A61B 5/11* (2006.01)
*G16H 20/30* (2018.01)
(Continued)

(52) U.S. Cl.
CPC ............ *G16H 20/30* (2018.01); *A61B 5/1118* (2013.01); *A61B 5/1123* (2013.01); *A61B 5/4866* (2013.01); *A61B 5/6898* (2013.01); *G01C 22/00* (2013.01); *G01C 22/006* (2013.01);
(Continued)

(58) Field of Classification Search
CPC .... G01C 22/006; G01C 21/165; G01C 22/00; G01C 21/20; G06F 3/017; G06F 19/00; G06F 19/3418; A43B 3/0005; G05D 1/0278; G08G 1/0969; G01S 19/19; G01T 1/026; A61B 5/6898; A61B 5/1118; A61B 5/1123; G01P 15/02
USPC .......... 702/160; 345/156; 324/160; 340/989; 455/556.1, 456.1; 250/370.01
See application file for complete search history.

(56) References Cited

U.S. PATENT DOCUMENTS 6,882,955 B1 * 4/2005 Ohlenbusch ......... A43B 3/0005
324/160
7,057,551 B1 6/2006 Vogt
(Continued)

FOREIGN PATENT DOCUMENTS

WO WO-2013/096954 A1 * 6/2013 ......... G06F 19/3418
WO WO 2013/109762 A1 7/2013
(Continued)

*Primary Examiner* — Regis J Betsch
*Assistant Examiner* — Kaleria Knox
(74) *Attorney, Agent, or Firm* — von Briesen & Roper, s.c.

(57) ABSTRACT

The method for calculating the activity of a user, said method being implemented by a personal activity monitor intended to be securely associated with the body of the user, and by a smartphone equipped with a geolocation function, exchanging data over a wireless connection, the method comprising the steps of:

-a- the activity monitor detects and counts the steps of the user,
-b- the smartphone determines a first geolocation at a first time,
-c- the smartphone determines a second geolocation at a second time,
-d- one of the two devices calculates a distance traveled between the two geolocations, (Continued)

-e- one of the two devices calculates, based on the distance traveled and the number of steps taken between the two geolocations, the average stride and/or average step of the user.

14 Claims, 5 Drawing Sheets

(51) Int. Cl.
  G01S 19/19 (2010.01)
  G01S 19/49 (2010.01)
(52) U.S. Cl.
  CPC .............. G01P 15/02 (2013.01); G01S 19/19 (2013.01); G01S 19/49 (2013.01)

(56) References Cited

U.S. PATENT DOCUMENTS

| | | | |
|---|---|---|---|
| 2006/0028429 A1* | 2/2006 | Kanevsky | G06F 3/017 345/156 |
| 2007/0075251 A1* | 4/2007 | Doughty | G01T 1/026 250/370.01 |
| 2007/0213092 A1* | 9/2007 | Geelen | G08G 1/0969 455/556.1 |
| 2013/0021174 A1* | 1/2013 | Silzer, Sr. | G05D 1/0278 340/989 |
| 2013/0046463 A1* | 2/2013 | Bengtson | G01C 21/165 701/500 |
| 2013/0138394 A1* | 5/2013 | Shiga | G01C 22/006 702/160 |
| 2013/0196688 A1* | 8/2013 | Lu | G01S 19/19 455/456.1 |
| 2013/0231889 A1* | 9/2013 | Hrybyk | G01C 21/20 702/141 |
| 2013/0325404 A1 | 12/2013 | Yuen et al. | |
| 2014/0300490 A1* | 10/2014 | Kotz | G06F 19/3418 340/870.3 |
| 2015/0285659 A1* | 10/2015 | Curtis | G01C 22/006 702/97 |

FOREIGN PATENT DOCUMENTS

| | | | | |
|---|---|---|---|---|
| WO | WO2013109762 A1 * | 7/2013 | | G06F 19/00 |
| WO | WO 2015152921 A1 * | 10/2015 | | G01C 25/00 |

* cited by examiner

METHOD FOR CALCULATING THE ACTIVITY OF A USER

CROSS-REFERENCE TO RELATED APPLICATION

This application claims priority under the Paris Convention to French Patent Application No. 14 54498 filed on May 20, 2014.

FIELD OF THE DISCLOSURE

The present invention relates to methods for calculating the activity of a user, particularly methods for determining the type of activity performed by the user and the associated caloric expenditure.

BACKGROUND OF THE DISCLOSURE

More particularly, the invention relates to a method for calculating the activity of a user by using a combination of a personal activity monitor and a smartphone (or equivalent) equipped with a geolocation function. For an individual referred to as a "user", the term "activity" as used here covers walking, running, walking a dog, bicycling, golf, horseback riding, ball sports, racket sports, as well as riding a scooter, a skateboard, or any non-motorized travel or even motorized travel.

A personal activity monitor is a small and very lightweight device that the user can carry close to the body, for example at the wrist or at the belt, or in any suitable location where said monitor can be securely associated with the body of the user.

There are known activity monitors which measure the activity of a user, such as those disclosed in US2013 0325404, particularly those having an embedded accelerometer. This type of activity monitor can thus detect the steps of the user (if the user is running, this is called the 'stride') and therefore count the steps and/or strides of a user when he or she is moving about on foot and/or walking and/or running. This type of activity monitor also tracks the corresponding distance covered by the user, calorie expenditure, and ascents/descents.

Although the estimation of the number of steps is relatively accurate, the evaluation of the distance traveled can be problematic and imprecise because the distance traveled is obtained by multiplying the number of steps (or strides) by a predefined average step value. Statistical surveys show that the average step (stride) of individuals can vary from 0.6 m to 2.5 m which represents a wide range. Even if the predefined step value can be estimated based on user height (assuming that the user can enter this into the activity monitor), calculation of the distance traveled remains inaccurate, especially when the user is performing a variety of activities (strolling, brisk walking, light jogging, sustained jogging, fast running) and given the natural diversity among individuals. Double integration of acceleration signals would also be affected by imprecision.

The estimation of ascents/descents or calorie expenditure is also affected by imprecision.

Some have proposed to include a GPS receiver in this type of activity monitor, but this raises two important issues: firstly, a GPS receiver is a heavy power consumer and this greatly reduces the autonomy of the activity monitor, and secondly, integration of such a GPS receiver results in an increase in the dimensions and weight of the activity monitor.

There is therefore a need to improve the reliability of the 'distance traveled' information evaluated and displayed by such personal activity monitors.

SUMMARY OF THE DISCLOSURE

To this end, the invention provides a method for calculating the activity of a user, said method being implemented by a portable electronic first device (1) consisting of a personal activity monitor intended to be securely associated with the body of the user, and by a portable electronic second device (2) consisting of a smartphone equipped with a geolocation function, the first and second devices being configured to exchange data over a wireless connection, the method comprising the steps of:
-a- the first device detects and counts almost continuously the steps or cycles of the user,
-b- the second device determines the current geolocation of the user at a first time (T1), which constitutes the first geolocation (A1),
-c- the second device determines the current geolocation of the user at a second time (T2), which constitutes the second geolocation (A2),
-d- one of the two devices (1,2) calculates a first distance traveled (D12) between the first and second geolocations (A1, A2),
-e1- deducing, based on the levels of acceleration experienced between the first and second times (T1, T2) and on the first distance traveled D12, the current type of activity among a plurality of types of activity including walking, running, bicycling, horseback riding, racket sports, and golf,
-e2- deducing a calculation of the calorie expenditure between the first and second times,
-e3- if the current type of activity is walking, running, or bicycling, one of the two devices (1,2) calculates, based on said first distance traveled D12 and the number of steps taken between the first and second geolocations (A1, A2), the average stride and/or average step and/or average gear ratio of the user between the first and second geolocations.

With these arrangements, the first device can personalize and refine its own data concerning that particular user about the type of activity performed and the average stride and/or average step and/or average gear ratio of that particular user.

Further, the first device can carry on assessing the traveled distance in a reliable fashion, even though the geolocation is temporarily not available, for example in the following cases: Smartphone (second device) shut-off, Smartphone forgotten at home, underground gymnastics premises with poor GPS satellites signals availability.

In preferred embodiments of the invention, it is possible that one or more of the following arrangements may also be used.

In steps -b- and -c-, preferably the second device determines the current geolocation of the user in response to a request from the first device; determination of the geolocation is thus initiated by the first device, such that use of the GPS tracking resource can occur according to the intensity and level of user activity, which allows contacting the GPS resource in the most optimized way, and in particular eliminating such contact if the activity monitor is stationary and thus minimizing power consumption on the smartphone side.

The first device may send geolocation queries to the second device based on one or more of the following predetermined criteria: in particular at the beginning or end of activity, and/or in case of a change of activity intensity level, and/or after a predefined number of steps since the last query, and/or after a predefined length of time since the last query. The activity monitor thus continuously adapts the frequency of queries towards the GPS resource, minimizing power consumption by both the electrical activity monitor and the smartphone.

In step -d-, it is preferably the second device 2 that calculates the first distance traveled D12 and that sends this to the first device 1, the latter performing steps -e1-, -e2-, and -e3-; the distance calculation operations, requiring non-trivial operations, are thus performed by the smartphone and not by the activity monitor.

In step -d-, the first distance traveled D12 is calculated as a geometric distance between the first and second geolocations (A1, A2). The second device thus performs a simple calculation of the distance as the crow flies between the geographic coordinates of two geolocations.

In addition, the geolocation function of the second device 2 may have access to a mapping database, and the second device 2 calculates, by means of the access to the mapping database, the actual distance traveled by the user along the map route between the first and second geolocations A1, A2. This is an accurate calculation using the most likely path followed by the user (whether pedestrian or cyclist).

The method may further comprise, between steps -b- and -c-, a step of determining one or more intermediate geolocations between the first and second geolocations, the distance calculation then summing the distances between successive geolocations. One can thus limit the amount of data exchanged between the first device and the second device, the first device merely requesting from the second device the total distance traveled, for example at the end of the activity in question.

The geolocation function of the second device may be provided by a GPS receiver. Geolocations can thus be determined in a highly accurate manner.

The geolocation function of the second device 2 may be provided by the determination of antenna signals from antennas of known location, particularly the antennas of cellular telephone networks, antennas of Wifi hotspots, or the equivalent. It is thus possible to obtain the geolocation even without a GPS receiver or to supplement the GPS receiver when the receiver is not receiving satellite signals.

The antenna signals can be complemented in the second device by the use of a magnetometer or gyroscope. This enables more accurate estimation of the position when satellite signals are not available or there is no GPS receiver.

According to an alternative solution, after each geolocation determination, the second device 2 sends the geographic coordinates determined in steps -b- and -c- (meaning the first and second geolocations) to the first device, said first device can then perform steps -d-, -e1-, -e2-, and -e3-; the smartphone can thus provide the geolocation information to the first device (the activity monitor) by a very simple method, which will allow the first device itself to apply corrections to the average stride of the user.

The second device can send to the first device, spontaneously at regular intervals (Ti), the geographic coordinates of the user's current geolocation; thus, the geographic coordinates are regularly available to the first device and said first device can calculate the distance traveled in each interval between successive positions, and deduce a correction for the average stride of the user in a simple manner. This provides a very simple method that can function without maps, and that uses a simple routine of a smartphone application.

In another alternative, steps -d-, -e1-, -e2-, and -e3- are performed by the second device, the first device thus not performing any complicated calculations and directly receiving the corrections to be applied to the average stride of the user concerned; the first device can then remain very simple in its functionalities, very light, and very small, with low power draw.

A database may be provided that relates a plurality of geolocation data and a type of user activity, in order to improve the determination of the average stride of the user. This provides additional clarification on the assumed activity, and the value of the average stride can be adapted to the type of activity: strolling, walking, jogging, running, racket sports, ball sports, horseback riding, golf, bowling, mushroom picking, hiking with ascents and/or descents, etc.

According to another object of the invention, an information system is provided for a user, comprising a portable electronic first device (1) consisting of a personal activity monitor (1) intended to be securely associated with the body of the user and without its own means of geolocation, and a portable electronic second device (2) consisting of a smartphone (2) equipped with a geolocation function, the first and second devices being physically independent (distinct) and configured to exchange data over a wireless connection, the first device being configured to measure the signals of acceleration experienced and to count almost continuously the user steps or cycles, the second device being configured to determine the current geolocation of the user at a first time (T1), which constitutes the first geolocation (A1), the second device being configured to determine the current geolocation of the user at a second time (T2), which constitutes the second geolocation (A2), the second device being configured to calculate a first distance traveled between the first and second geolocations A1, A2, the first device being configured to calculate, using said first distance traveled D12 and the number of steps taken between the first and second geolocations (A1, A2), the average stride and/or average step and/or average gear ratio of the user between the first and second geolocations, whereby the first device can refine the average step and stride value or values for that particular user.

Other features and advantages of the invention will become apparent from the following description of several of its embodiments, given by way of non-limiting example and with reference to the accompanying drawings.

BRIEF DESCRIPTION OF THE DRAWINGS

In the drawings.

In the various figures, the same references designate identical or similar elements.

DETAILED DESCRIPTION OF THE DISCLOSURE

Figure 1:
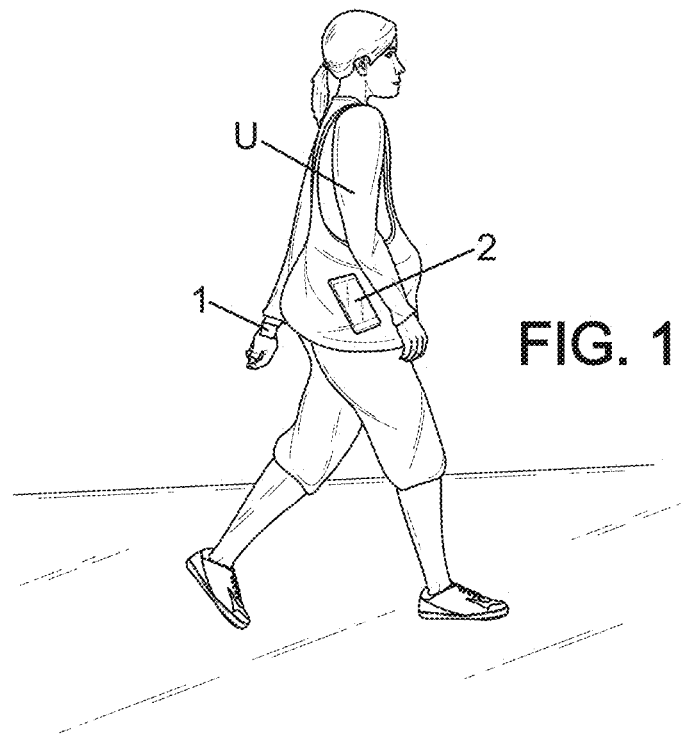
FIG. 1 shows a user equipped with an activity monitor and smartphone.

In FIG. 1, a user U is equipped with a first portable electronic device 1 and a second portable electronic device 2, which are able to communicate with each other.
Activity Monitor The first electronic device 1 may be in the form of an activity monitor, adapted to be securely associated with the body of the user, for example at the wrist. It can thus continuously detect and count the user's activity, by means of an accelerometer inside the housing of this activity monitor. Another term used for this kind of device is "activity tracker."

Specifically, in the example shown, the first portable electronic device 1 is in the form of an activity monitor, for example the "Pulse"™ product from Withings™, the Applicant. The activity monitor may be in the form of a small housing, with a display system that shows the activity. The activity monitor is able to provide information to the user about his or her physical activity, walking, running, sleeping, stair climbing, etc.

Figure 2:
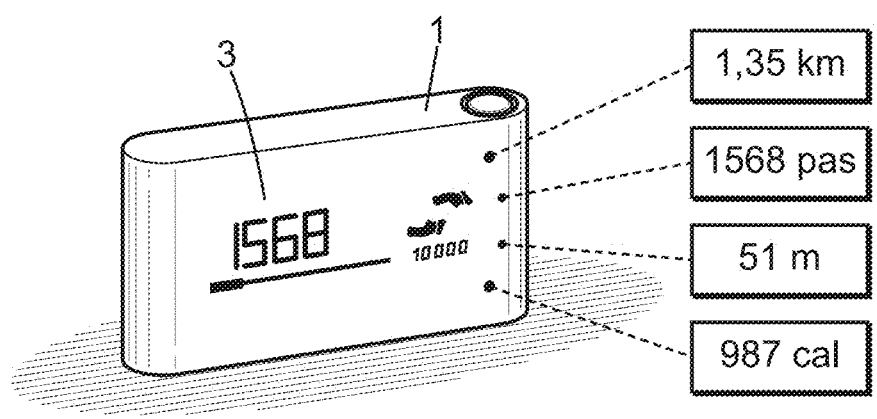
FIG. 2 shows the information evaluated and displayed by the activity monitor of FIG. 1.

FIG. 2 shows some of the information that the first device can provide to the user U, for example the distance traveled, the number of steps, elevation climbed, and number of calories burned.

The activity monitor 1 shown here weighs less than 10 grams, preferably less than 8 grams, even more preferably less than 6 grams. Its dimensions are particularly small, the thickness being at most equal to 8 mm, the width at most equal to 43 mm, and the height at most equal to 22 mm.

According to one solution, the first electronic device 1 may be in the form of some other device incorporating an activity monitor, such as a wristwatch named «Activité™» or «Activité Pop™» from the Applicant Withings™, and in this case, the first device weighs less than 50 grams, preferably less than 40 grams.

Alternatively, the first electronic device 1 may be in the form of instrumented eyeglasses, or smart glasses such as "Google Glass"™. It should be noted that the first device may also be integrated into another device on the user, such as in an earbud, hearing aid, smart necklace, digital identification tag inserted under the skin, etc.

In general, the first electronic device 1 is adapted to be substantially secured to at least a portion of the body of said user during said method, for example worn on the belt of the user, or on a bracelet attached to the wrist; analysis of the signals provided by the accelerometer allows measuring the acceleration signals, evaluating the intensity of the signals and their more or less periodic aspects, and accurately detecting the steps made by the user U, and strides even more so.

In general, the amplitude, temporal, and frequency characteristics of the acceleration signals allow recognizing the type of activity performed by the user, namely whether the user is walking, running, bicycling, horseback riding, playing golf, etc. Determining the type of activity allows more precise calculation of calorie expenditure.

The activity monitor 1 is preferably deprived of a GPS receiver.
Smartphone

The portable electronic second device 2 consists here of a smartphone. Said portable electronic second device 2 may be located, for example, in a handbag carried by the user as shown in FIG. 1, or in a pocket, backpack, or elsewhere, therefore not necessarily worn close to the body.

The second device 2 could also be in the form of a tablet, phablet, nettop, or PDA, accompanying the user U.

The second device 2 has larger dimensions than those of the first device, generally has a screen measuring several inches diagonally, and generally comprises a plurality of functionalities, including basic routines (in the operating system) and high-level applications. In the context of the invention, the functionalities of interest concern the geolocation capabilities available in the second device 2.

According to one embodiment, the geolocation function is provided by a GPS receiver configured to receive and decode signals from GPS positioning satellites (known per se). Of course, "GPS" is also understood to refer to equivalent systems such as GLONASS and Galileo.

Additionally or alternatively, the second device 2 may rely on analysis of signals from terrestrial antennas of known geolocation. More specifically, the geographic location of all wireless relays is listed in a database, and the geographic location of all cell antenna towers of all cellular telephone networks is also listed in a database. By analyzing the identification of the antennas from which signals are received by the second device, using triangulation in favorable cases and/or evaluating the strength of the received signals, the geolocation of the second device can be determined relatively accurately without directly receiving GPS satellite signals.

According to an additional function, the analysis of GPS signals and/or the analysis of terrestrial antenna signals can also be complemented by the use of a magnetometer or gyroscope; these devices provide information about relative displacement, particularly the direction, which is useful in case the other signals mentioned above are not always available or have momentary interruptions or are of degraded quality.

Note that in the context of the invention, the smartphone 2, the user U, and the activity monitor 1 are considered to be very close to each other, and the differences between the geographic locations of the three entities can be neglected.
Communication and FIG. 3

Both devices (1,2) are able to connect to one another and exchange data, preferably over a wireless connection. The wireless connection can be established by a Bluetooth™, WiFi, Zigbee, RFID, or equivalent interface.

The smartphone 2 is further provided with the ability to communicate with a cellular telephone network (optionally with Internet access), which optionally provides it with access to one or more databases of mapping data (geo-maps) which will be discussed further below.

Figure 3:
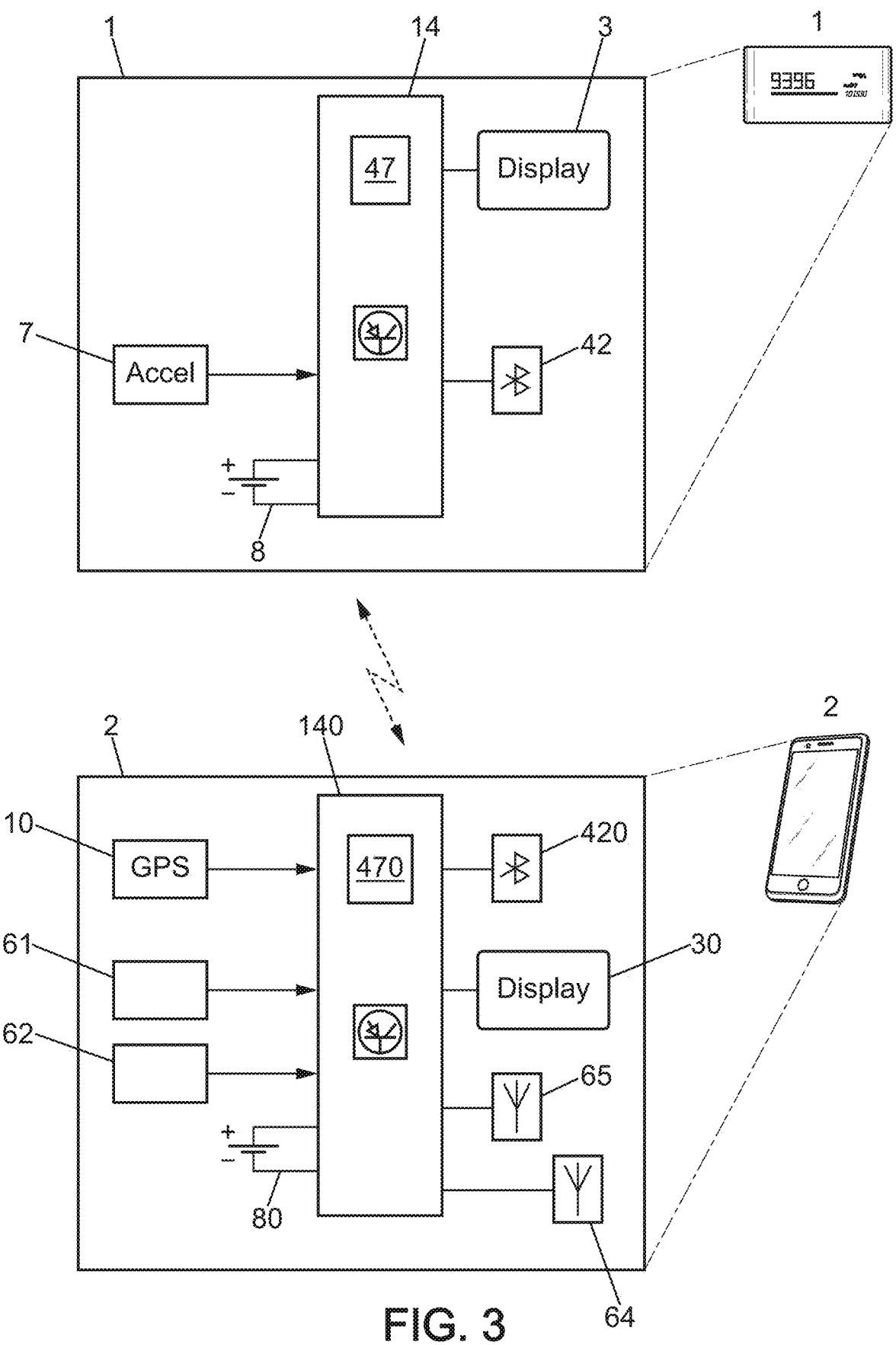
FIG. 3 shows a functional block diagram of the activity monitor and smartphone.

As illustrated in FIG. 3, said first device 1 comprises a computation unit 14, a Bluetooth™ communication interface 42, a display 3, and a multi-axis acceleration sensor 7. The acceleration sensor 7 can detect accelerations experienced by the device, from which are estimated the accelerations experienced by the user. The acceleration information is used to estimate the number of steps taken by the user.

The display 3 is configured to provide the user with a plurality of information, particularly the number of steps taken and distance traveled in a counter. This counter may reset daily or at some other period depending on the configuration specified by the user. The display may be a touch display, which allows the user U to scroll through different types of information.

The computation unit 14 processes the data via a processor which comprises memory 47 and which manages in said memory the data directly measured by the first device 1 or for example received from another device such as the smartphone 2. The first device 1 also stores in said memory 47 the different average step values for the user in possession of said device, and according to the different types of activity.

The computation unit 14 is powered by an embedded power source 8, for example a rechargeable battery as shown here, which supplies power to all the embedded elements.

As is also illustrated in FIG. 3, said second device 2 also comprises a computation unit 140.

The smartphone 2 may advantageously comprise a GPS receiver 10 connected to the computation unit 140, from which the user's position at any moment can be precisely calculated.

Additionally, the second device 2 may comprise a magnetometer 61, a gyroscope 62, or even a mini gyroscope platform.

The smartphone 2 comprises an operating system, known per se, for example such as Android™ or iOS™; this operating system may include standard services (basic routines available for all applications), in this case a geolocation service. This geolocation service makes use of the aforementioned available resources, GPS receiver, identification of terrestrial antennas of known geographical location, magnetometer, gyroscope, etc. The smartphone 2 may comprise a number of applications that can be launched by the user or that run continuously in the background, some of them using the geolocation service.

The first device 1 may contact the geolocation service of the operating system of the second device 2 directly, or it may contact a higher level application that uses the geolocation service and mapping elements.

The computation unit 140 comprises a display 30 configured to provide the user with a plurality of information as is known, a Bluetooth™ communication interface 420, and a memory 470 where a plurality of data are stored and managed.

The second device 2 also comprises another communication antenna 64 for a cellular telephone network and yet another communication antenna 65 for a WLAN or WiFi type of local area network.

The computation unit 140 is powered by an embedded power source 80, in the current case for example a rechargeable battery that powers all embedded elements.

Average Step Correction—FIGS. 4-8

In the embodiments described below, the first device 1 measures accelerations, and continuously detects and counts the user's steps (step -a- of the method). In addition, it stores in memory at least one predetermined value for the average step of the user during walking conditions; advantageously, the first device can store several predefined values MK0-U in memory (see FIG. 10 and associated comments below), for the average step for each of the identified user activities (strolling, fast walking, slow jogging, running, sprinting, hiking uphill and downhill, etc).

Note that the invention can also be applied in an activity other than running or walking, for example bicycling, horseback riding, racket sports, ball sports, etc. In the case of bicycling, the first device 1 continuously detects and counts the pedal strokes of the user.

Advantageously according to the invention, the first device will attempt to further customize these predefined values as will be described in detail below.

Figure 4:
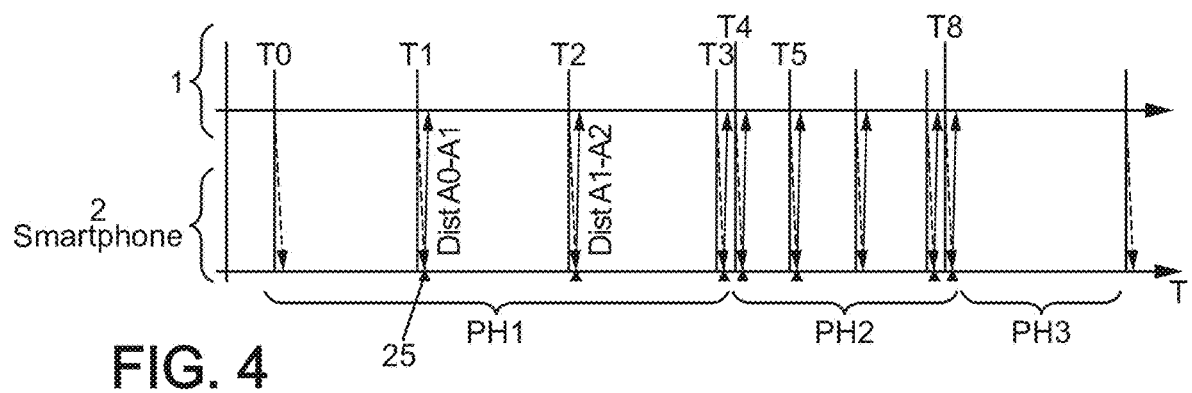
FIG. 4 shows a timing diagram of the exchanges between the activity monitor and smartphone.

According to a first embodiment, in the example shown in FIG. 4, it is the first device 1 that initiates the exchange between the first device 1 and the second device 2. In the example shown, the user's route includes a walking phase PH1, a running phase PH2, and a resting phase PH3 (not moving).

The first device successively sends geolocation requests at times T1, T2, . . . , Tn to the second device 2.

At each request, the second device 2 determines the geolocation of the current position, which means the successive geolocations A1, A2, . . . , An. The geolocation determination operation at points A1 and A2 corresponds to steps -b- and -c- of the method.

In addition, after each geolocation determination operation, the second device 2 calculates the distance traveled since the geolocation previously determined, this calculation operation (step -d-) being represented by the triangle 25 and detailed further below.

For example, at time T2, the second device 2 calculates the distance between points A1 and A2, denoted 'DistA1-A2', and also called the 'first distance traveled' and denoted D12, and sends this distance D12 to the first device.

The first device 1 can then calculate (step -e3-) the specific average step M12 of the user which corresponds to the ratio D12/N12, N12 being the number of steps detected and counted between the query at time T1 and the query at time T2. The use by the activity monitor of the value of the specific average step M12 will be detailed further below.

The above operations can, of course, be repeated recursively.

The first device 1 may also use this opportunity to update the total distance by adding the distance received D12 to the known total.

A special case concerns certain types of activities that are practiced within a relatively small area, such as racket sports, ball sports, or show jumping, and in this case the distance calculations give very low results because the user often moves back and forth over small distances; this is put to good use by determining that it is indeed a type of activity restricted to a specific field. The size of the field allows clarifying the type of activity, such as squash, badminton, tennis, handball, basketball, football, rugby, or golf. In the case of golf, the signal that is characteristic of a swing is also used to determine this specific type of activity.

In the case of practicing jogging on a treadmill in a gym room, the recognition of the activity type is important to avoid false calculations of an average stride close to 0 knowing that the GPS location does not vary much when the user U runs on the treadmill.

In the case of the bicycle, it is not the average step that the system calculates but the gear ratio, meaning the distance traveled per pedal stroke. The pedaling speed is also used along with the gear ratio to correct the calculation of calorie expenditure.

Note that geographic coordinates can also include an elevation coordinate, and in this case the distance between points A1 and A2 also includes the elevation gain or loss. The first device 1 can use this to consolidate the information into the net elevation gain, and to refine the calculation of calorie consumption.

The operations described above are repeated at time T3 for the portion of the path between points A2 and A3, then again repeated between points A3 and A4 at time T4, and so on.

The first device 1 may issue requests on a regular basis. Advantageously, the first device will issue queries on the basis of one or more of the following predetermined criteria:
at the beginning or end of the activity,
and/or in case of a change in the level of activity,
and/or after N1 steps since the last query, and/or after X1 minutes since the last query according to the detected level of activity, the frequency being proportional to the intensity of the detected activity.

In FIG. 4, one can see that the querying frequency is higher in period PH2 where the user U is running, while it is slower in the period PH1 where the user is walking, and there are no more queries during the resting phase PH3.

For the criterion concerning the number of steps N1 that will trigger a new query, one can take parameter N1 within a range of 50 to 200 steps, typically choosing N1=100 steps.

Similarly, for the criterion concerning the time since the last query, one can take parameter X1 within a range of 30 s to 180 s, for example 60 s, 90 s, or 120 s.

One will note that the activity monitor can submit additional geolocation queries, for example with each change of activity level or type, as is illustrated at times T4 and T8 in FIG. 4.

For calculating the distance traveled (step -d- of the method), according to a first solution the second device 2 calculates the distance traveled A1-A2 between two times T1-T2, geometrically, by extrapolating between two geolocations along a straight line (distance as the crow flies). The second device 2 sends this information to the first device 1 which calculates, using the number of steps between positions A1 and A2, the average stride of the user between the two positions concerned. This solution is quite acceptable if most of the path segments between points Ai and Ai+1 are substantially straight, which is usually true in urban conditions.

Figure 9:
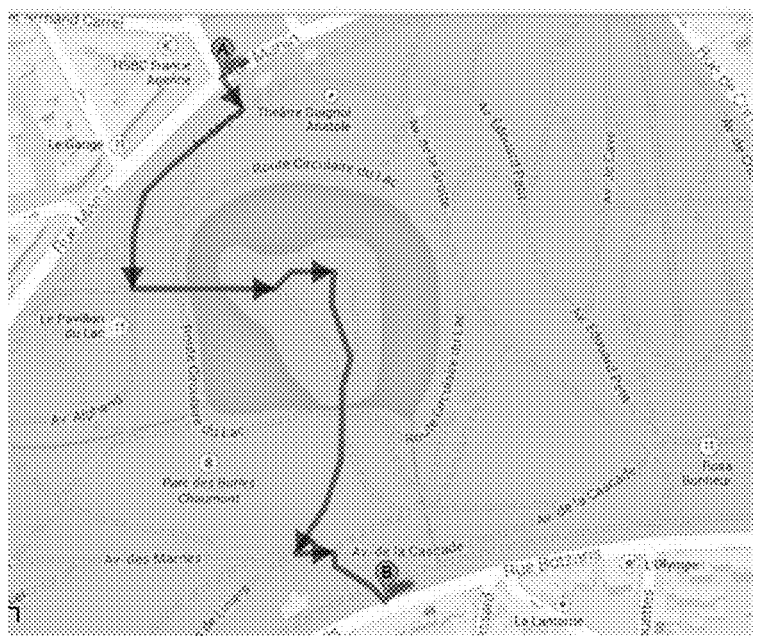
FIG. 9 shows an alternate route followed by a user.

According to a second solution for calculating the distance traveled, the second device 2 is provided with a mapping function, preferably used in this case by setting the mode to 'walking'. By calculating the map route, the second device 2 determines which feasible path was followed by the user between the two geolocations Ai and Ai+1. The actual distance traveled by the user between the two geolocations can thus be calculated precisely, and in some cases this result may be quite different from a straight line, as illustrated in FIG. 9.

Note that the mapping calculation function can be performed locally on the smartphone or by a remote Web service called upon by the smartphone.

Using a mapping calculation of the distance allows longer times between queries from the activity monitor (larger X1 and/or N1), thereby reducing power consumption for this function and also reducing the amount of data exchanged.

Figure 5:
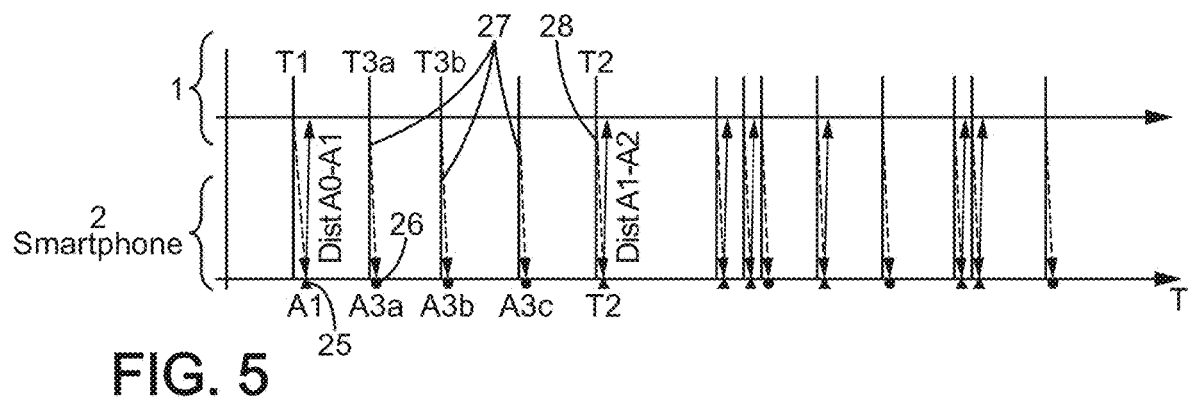
FIG. 5 shows a variant of the timing diagram of FIG. 4.

In a variant of the first embodiment, shown in FIG. 5, the queries from the first device 1 do not systematically result in calculating and returning the distance traveled. The first device 1 may request the distance traveled from time to time, but not with every query. This variant may be advantageous in the case where the second device 2 does not have any mapping function nor access to a mapping resource, and in this case it will calculate the distances by line segments between the various intermediate points A3a, A3b, A3c, without calling upon a mapping resource. The sum of the segment distances then gives the distance between two moments T1,A1 and T2,A2 where the first device requests the distance traveled. The intermediate points A3a, A3b, A3c can be considered as waypoints that serve to calculate a distance traveled that accurately represents the actual route taken by the user U.

In this case there is therefore a simple query type 27 such as a 'track' position query, and a complete query type 28 for requesting the result of calculating the distance traveled.

Figure 7:
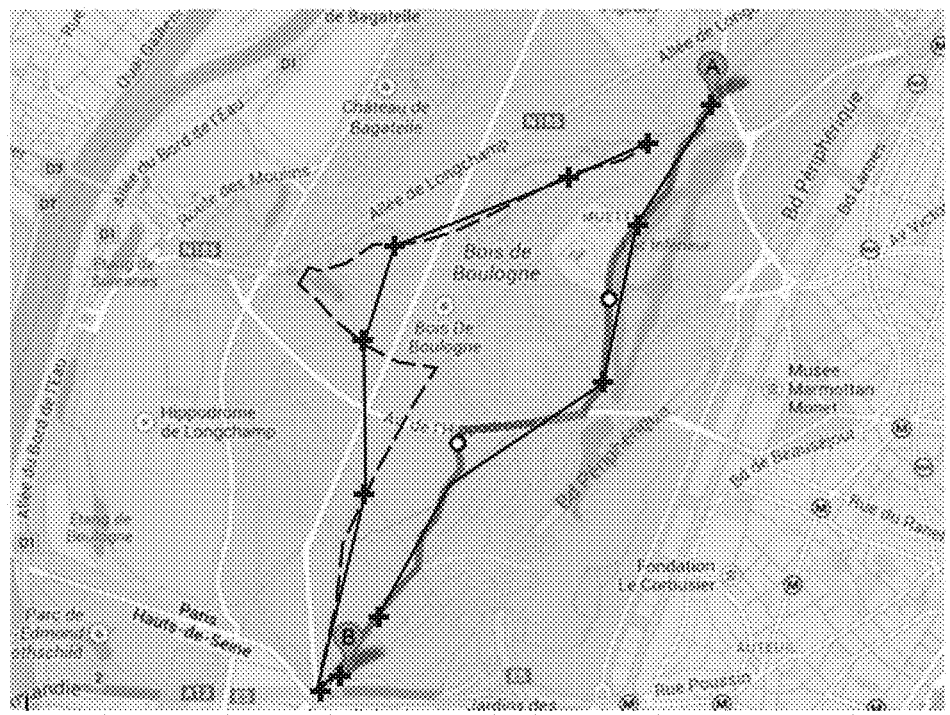
FIG. 7 shows a route followed by a user.
Figure 8:
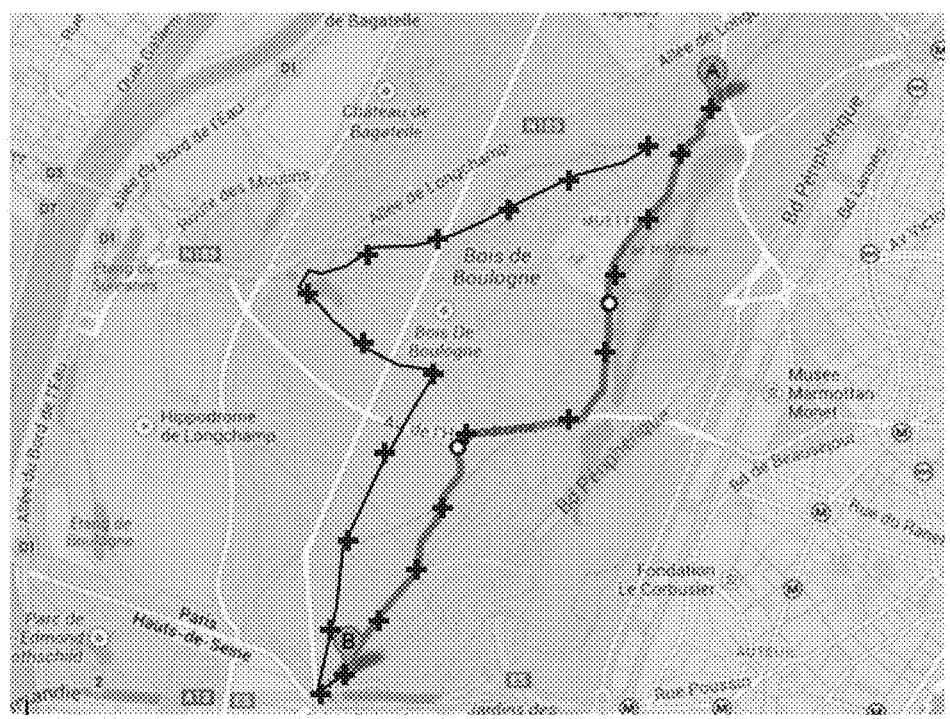
FIG. 8 shows a variant of the route of FIG. 7.

FIG. 7 shows a case where the geolocation determinations are infrequent and where the use of a mapping aid helps avoid errors in interpolation (solid line connecting the crosses); for the same path, FIG. 8 illustrates a case where the geolocation determinations are more frequent and the use of a mapping aid is not required, and in addition the total distance traveled can be updated in near real time from the data received from the smartphone.

Figure 6:
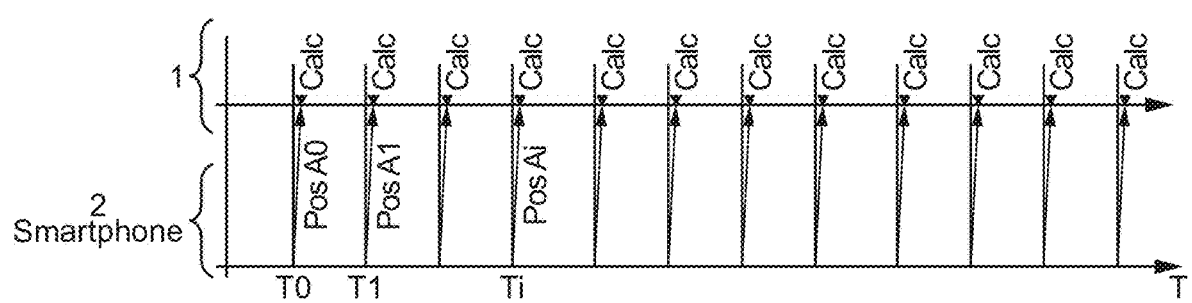
FIG. 6 shows another variant of the timing diagram of FIG. 4.

In a second embodiment represented in FIG. 6, the first device 1 does not initiate the exchanges, it simply receives information regularly and spontaneously sent by the second device 2.

Specifically, the user's current position is sent to the first device 1 by the second device 2. The first device 1 thus calculates the distance traveled A1-A2 between two times T1,T2, by extrapolating between two geolocations along a straight line, and repeats the operation for the path between points A2 and A3, then A3 and A4, and so on.

The first device 1 calculates, using the number of steps between positions A1 and A2, the average stride M12 of the user between the two positions concerned. The activity monitor 1 may or may not use the information received from the smartphone depending on requirements, for example depending on the actual activity of the user U.

The logic for sending geolocation information from the smartphone 2 may be based on a predetermined time period (FIG. 6), or the interval between the transmission of geolocation data may depend on the actual displacement of the smartphone, for example whenever the smartphone has moved at least 10 meters.

According to yet another embodiment not shown in the figures, the functionality supported by the first device is simplified. In this case, as is known, the first device 1 regularly sends to the second device 2 the number of steps of the user for statistical purposes and for displaying to the user on the display 30. This data 'upload' can be done with each new Bluetooth connection, or according to a certain schedule, for example every five minutes.

It should be noted that some of the data uploaded by the activity monitor to the smartphone are time-stamped, and advantageously the clocks of the activity monitor and smartphone are synchronized.

In the present case, the second device 2 not only calculates the distance traveled A1-A2 between two times T1, T2, but it also determines the specific average stride M12 of the user, this value M12 being obtained as above based on the distance traveled A1 and A2 between two times T1, T2 and on the number of steps N1 received from the activity tracker 1. This information on the specific average stride M12 is sent back to the first device 1 so it can refine the average step value of the user.

As a variant, the second device 2 comprises (or accesses) a pre-established database relating geolocation and type of user activity. When the geolocation of the user is determined by the second device 2, the database on physical activities in relation to geolocation is queried to determine the most likely activity. This parameter is included in order to make corrections to the average stride of the user. Geolocation data can thus indicate that the user U is walking along a conventional street, or along a path in a park, or on a mountain trail, or on the track of a stadium, etc.

Figure 10:
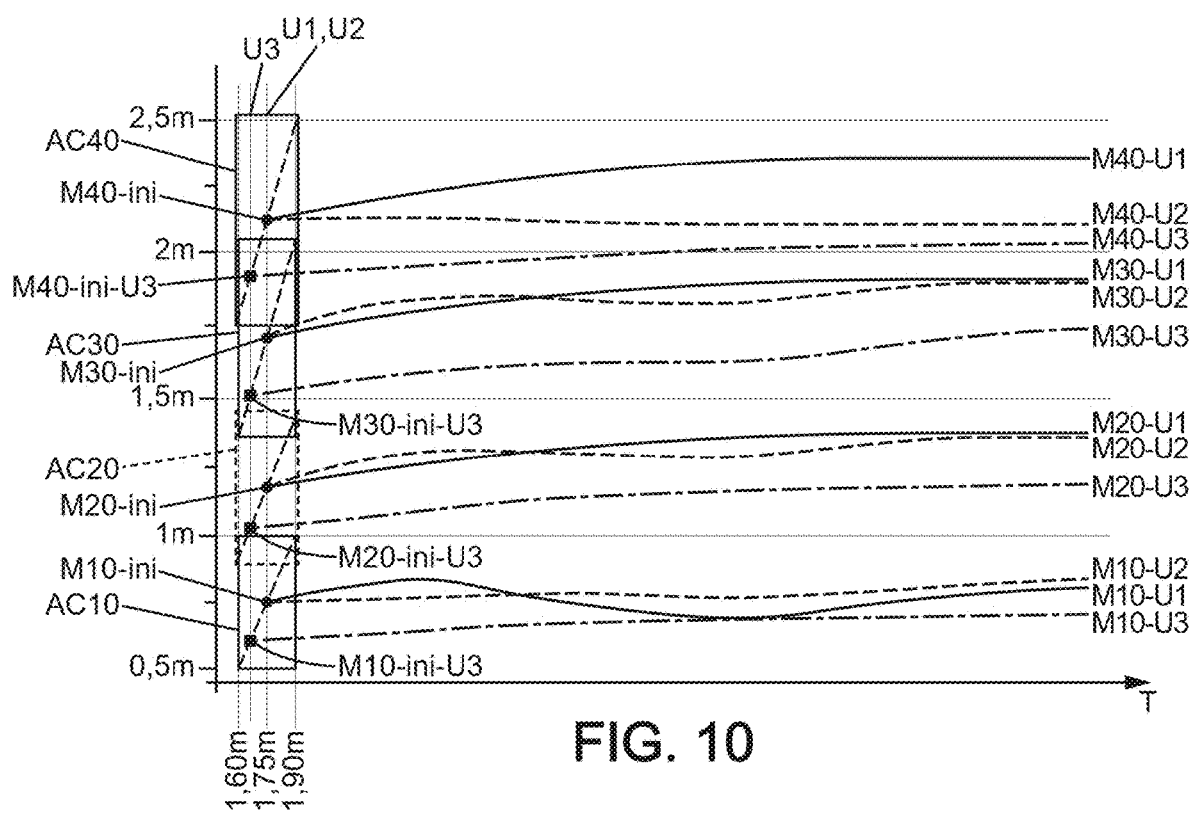
FIG. 10 shows curves that illustrate how multiple activity monitors gradually adjust respectively the average step/stride values for individual users.

Referring to FIG. 10, four types of activity are defined as an example: a leisurely stroll AC10, a brisk walk AC20, jogging AC30, and running AC40.

Also defined are three different users: U1 and U2 whose heights are not known to their respective activity monitors or have not been specified in the web interface, and a third user U3 whose height is known to her activity monitor: 1.67 m.

As indicated above, the average step/stride varies widely from one activity to another and from one individual to another. However, for the first activity AC10 of a leisurely stroll, one can assume that the statistical average step varies from 0.5 m for a person 1.60 m in height to 1 m for a person 1.90 m in height. Similarly, for the brisk walking activity AC20 one can assume that the statistical average step varies from 0.8 m for a person 1.60 m in height to 1.4 m for a person 1.90 m in height. Similarly, for the jogging activity AC30 one can assume that the statistical average stride varies from 1.2 m for a person 1.60 m in height to 1.9 m for a person 1.90 m in height; for AC40 (running), the statistical average stride varies from 1.7 m for a person 1.60 m in height to 2.5 m for a person 1.90 m in height.

In the absence of information on the user height, the activity monitor will take initial values corresponding for example to the statistical value of 1.75 m, which gives the points M10-ini, M20-ini, M30-ini, and M40-ini indicated by small circles in FIG. 10.

In the case of user U3, the starting values can be more accurate, giving points M10-iniU3, M20-iniU3, M30-iniU3, and M40-iniU3, indicated by small squares in FIG. 10.

Subsequent usage of the activity monitor 1 by each user U1, U2, U3 allows refining these initial values so they are customized for the user concerned.

For each user (for example U1), each new calculation of the specific average step M12 from the calculations described above is first classified into one of the types of activity (for example AC10) and then incorporated into the old known value M10-U1 using a moving average digital filter. As a result, the average value M10-U1 changes over time and becomes a specific value linked to the user U1.

For this user U1, four curves M10-U1, M20-U1, M30-U1, M40-U1 are obtained which converge to the average personal step/stride values.

The same thing occurs for user U2 who is carrying his own activity monitor, which although starting from the same initial values as for U1, evolves to other asymptotic values with curves M10-U2, M20-U2, M30-U2, M40-U2.

Personalized knowledge of parameters MK0-Ui for the step/stride values by type of activity allows the activity monitor to calculate the distance traveled in a reliable manner, even in the absence of a nearby smartphone; indeed, it should be noted that this system functions by learning and that after the learning phase for a personal activity monitor used by one user, the calculation of the distance traveled is reliable even when the user is only carrying his or her personal activity monitor (and not carrying a smartphone).

It should also be noted that the correction by geolocation is self-adaptive. For example, if an activity monitor is used by someone other than the usual person, then the average step/stride values will gradually be corrected to reach the values specific to the new user.

According to a more general aspect not necessarily related to a walking or running activity, after step -d- of determining the distance traveled, the proposed method implements step -e-, which can be defined in three steps:
-e1- based on the acceleration levels experienced between the first and second times (T1, T2) and on the first distance traveled D12, the type of current activity is deduced from among a plurality of types of activity comprising walking, running, bicycling, horseback riding, racket sports, and golf, this non-limiting list already having been mentioned above, the determination being done by either the personal activity monitor or the smartphone depending on the case, as indicated above,
-e2- from this, a calculation of the calorie expenditure between the first and second times is deduced, this calculation being done by either by the personal monitor activity or the smartphone depending on the case, as indicated above,
-e3- if the current type of activity is walking, running, or bicycling, the average step (if walking) and/or the average stride (if running) and/or the average gear ratio (if bicycling) is calculated.

Note that for the case of running laps within an enclosed stadium, the geolocation polling frequency may be increased in order to obtain at least two or more points along the circumference of the track.

For the particular case of horseback riding, the first device 1 can detect and recognize the characteristic amplitudes and frequencies of the acceleration signals involved when riding a horse. The impact of the four feet of the horse on the ground causes different frequency components than when a human is running or walking. The obtaining of the distance traveled, as explained above, by the second device 2 allows confirming the activity of horseback riding, particularly for the faster gaits of the horse (fast trot or gallop). Recognition of the "horseback riding" type of activity also allows a more accurate calculation of calories expended by the user, particularly according to the different gaits.

The invention claimed is:

1. A method for calculating the activity of a user, said method being implemented by a portable electronic first device consisting of a personal activity monitor intended to be securely associated with the body of the user and capable of detecting the accelerations experienced, and by a portable electronic second device consisting of a smartphone equipped with a geolocation function, wherein the first device comprises an acceleration sensor, a first computation unit and a memory, the memory storing different average step length values for respective different types of activity including at least walking and running, the first and second devices being physically independent and configured to exchange data over a wireless connection, the method comprising the steps of:
-a- the first device measures via the acceleration sensor signals of accelerations experienced at the first device and counts, at the first computation unit, substantially continuously, the steps or cycles performed by the user,
-b- the second device determines at a second computation unit, a current geolocation of the user at a first time, which constitutes the first geolocation,
-c- the second device determines at the second computation unit, a current geolocation of the user at a second time, which constitutes the second geolocation,
-d- one of the two devices calculates, respectively at one of the first or second computation unit, a first distance traveled between the first and second geolocations,
-e1- deducing, based on the levels of acceleration experienced between the first and second times and on the first distance traveled, the current type of activity among a plurality of types of activity including walking, running, bicycling, horseback riding, racket sports, and golf,
-e2- if the current type of activity is walking, running, or bicycling, one of the two devices calculates, by means of said first distance traveled and the number of steps taken between the first and second geolocations, a relevant updated length value of average stride and/or average step and/or average gear ratio of the user between the first and second geolocations, the first device updates in the memory the relevant step length value for a corresponding relevant type of activity concerning that particular user, thereby personalizing the different average step length values for respective different types of activity concerning that particular user, wherein, in steps -b- and -c-, the second device determines the current geolocation of the user in response to a request from the first device, and wherein the first device sends geolocation queries to the second device and is configured to minimize power consumption by adapting the frequency of geolocation queries according to one or more of the following predetermined criteria: at the beginning or end of an activity, and in case of a change in activity level, and after N1 steps since the last query, and after X1 minutes since the last query.

2. The method according to claim 1, wherein in step -d- it is the second device that calculates the first distance traveled and sends this to the first device, the latter performing steps -e1-, and -e2-.

3. The method according to claim 2, wherein in step -d-, the first distance traveled is calculated as a geometric distance between the first and second geolocations.

4. The method according to claim 2, wherein the geolocation function of the second device comprises access to a mapping database, and wherein the second device calculates, by means of the access to the mapping database, the actual distance traveled by the user along the map route between the first and second geolocations.

5. The method according to claim 1, wherein the method further comprises, between steps -b- and -c-, a step of determining one or more intermediate geolocations between the first and second geolocations, the distance calculation then summing the distances between successive intermediate geolocations.

6. The method according to claim 1, wherein the geolocation function of the second device is provided by a GPS receiver.

7. The method according to claim 1, wherein the geolocation function of the second device is provided by the determination of antenna signals from antennas of known location, including antennas of cellular telephone networks, and/or the antennas of Wifi hotspots.

8. The method according to claim 7, wherein the antenna signals are complemented in the second device by the use of a magnetometer or gyroscope.

9. The method according to claim 1, wherein, after each geolocation determination, the second device sends the geographic coordinates of the first and second geolocations to the first device, said first device then performing steps -d-, -e1-, and -e2-.

10. The method according to claim 9, wherein the second device sends to the first device, spontaneously at regular intervals, the geographic coordinates of the user's current geolocation.

11. The method according to claim 1, wherein steps -d- and -e2- are performed by the second device.

12. The method according to claim 1, wherein a database is provided that relates a plurality of geolocation data and a type of user activity, in order to improve the determination of the average stride of the user.

13. An information system for a user, comprising a portable electronic first device consisting of a personal activity monitor intended to be securely associated with the body of the user, and without its own means of geolocation, and a portable electronic second device consisting of a smartphone equipped with a geolocation function, the first and second devices being physically independent devices configured to exchange data over a wireless connection, wherein the first device comprises an acceleration sensor, a first computation unit and a memory, the memory storing different average step length values for respective different types of activity including at least walking and running, the first device being configured to measure the signals of accelerations experienced and to count substantially continuously the user steps or cycles, the second device being configured to determine the current geolocation of the user at a first time, which constitutes the first geolocation, the second device being configured to determine the current geolocation of the user at a second time, which constitutes the second geolocation, the second device being configured to calculate a first distance traveled between geolocations, the first device being configured to calculate, using said first distance traveled and the number of steps taken between the first and second geolocations, a relevant updated length value of the average stride and/or average step and/or average gear ratio of the user between the first and second geolocations, the first device updates in the memory the relevant step length value for a corresponding relevant type of activity concerning that particular user, thereby personalizing the different average step length values for respective different types of activity concerning that particular user, wherein, the second device is configured to determine the current geolocation of the user in response to a request from the first device, wherein the first device is configured to send geolocation queries to the second device and is configured to minimize power consumption by adapting the frequency of geolocation queries according to one or more of the following predetermined criteria: at the beginning or end of an activity, and in case of a change in activity level, and after N1 steps since the last query or after X1 minutes since the last query.

14. The method according to claim 1, wherein the first device is deprived of any geolocation function.

* * * * *